United States Patent
Barsan et al.

(10) Patent No.: US 9,091,669 B2
(45) Date of Patent: Jul. 28, 2015

(54) GAS SENSOR AND METHOD FOR PRODUCING THE SAME

(75) Inventors: Nicolae Barsan, Tübingen (DE); Udo Weimar, Tübingen (DE); Jens Kemmler, Wannweil (DE); Lutz Maedler, Bremen (DE); Suman Pokhrel, Bremen (DE)

(73) Assignees: Eberghard Karls Universitat Tubingen, Tubingen (DE); Universitat Breman, Breman (DE)

(*) Notice: Subject to any disclaimer, the term of this patent is extended or adjusted under 35 U.S.C. 154(b) by 220 days.

(21) Appl. No.: 13/809,631

(22) PCT Filed: Jul. 7, 2011

(86) PCT No.: PCT/DE2011/001417
§ 371 (c)(1),
(2), (4) Date: Jan. 11, 2013

(87) PCT Pub. No.: WO2012/006994
PCT Pub. Date: Jan. 19, 2012

(65) Prior Publication Data
US 2013/0111974 A1    May 9, 2013

(30) Foreign Application Priority Data
Jul. 13, 2010 (DE) .......... 10 2010 027 070

(51) Int. Cl.
*G01N 27/12* (2006.01)
*G01N 33/00* (2006.01)
(52) U.S. Cl.
CPC .......... *G01N 33/0009* (2013.01); *G01N 27/125* (2013.01); *G01N 27/127* (2013.01); *G01N 33/0047* (2013.01)

(58) Field of Classification Search
CPC ............. G01N 27/125; G01N 27/127; G01N 33/0047; H01L 2251/306; H01L 2251/308; H01L 51/442; H01L 21/02565; H01L 21/02628; H01L 31/1884
See application file for complete search history.

(56) References Cited

U.S. PATENT DOCUMENTS 6,565,811 B1 * 5/2003 Zaromb ........................ 422/88
7,083,880 B2 * 8/2006 Talin et al. ........................ 430/5

(Continued)

FOREIGN PATENT DOCUMENTS

| CN | 1542444 A | 11/2004 |
| JP | 5950353 A | 3/1984 |

(Continued)

OTHER PUBLICATIONS

Ghimbeu et al., "Detection of pollutant gases using electrostatic sprayed indium oxide and tin-doped indium oxide", Materials Chemistry and Physics 114 (2009), pp. 933-938.*

(Continued)

*Primary Examiner* — David A Rogers
(74) *Attorney, Agent, or Firm* — Nath, Goldberg & Meyer; Jerald L. Meyer; Stanley N. Protigal

(57) ABSTRACT

A gas sensor is used for detecting gas in the air, especially formaldehyde. The sensor comprises at least one gas-sensitive zone which is preferably a layer on a substrate and which contains the ternary compound $In_4Sn_3O_{12}$ as the gas-sensitive material. In order to produce the gas-sensitive zone, a flame spray pyrolysis (FSP) is carried out, organometallic compounds of indium and tin being used as the reactants. The gas sensor is especially suitable for online gas detection.

9 Claims, 2 Drawing Sheets

(56) References Cited

U.S. PATENT DOCUMENTS

Figure 1:
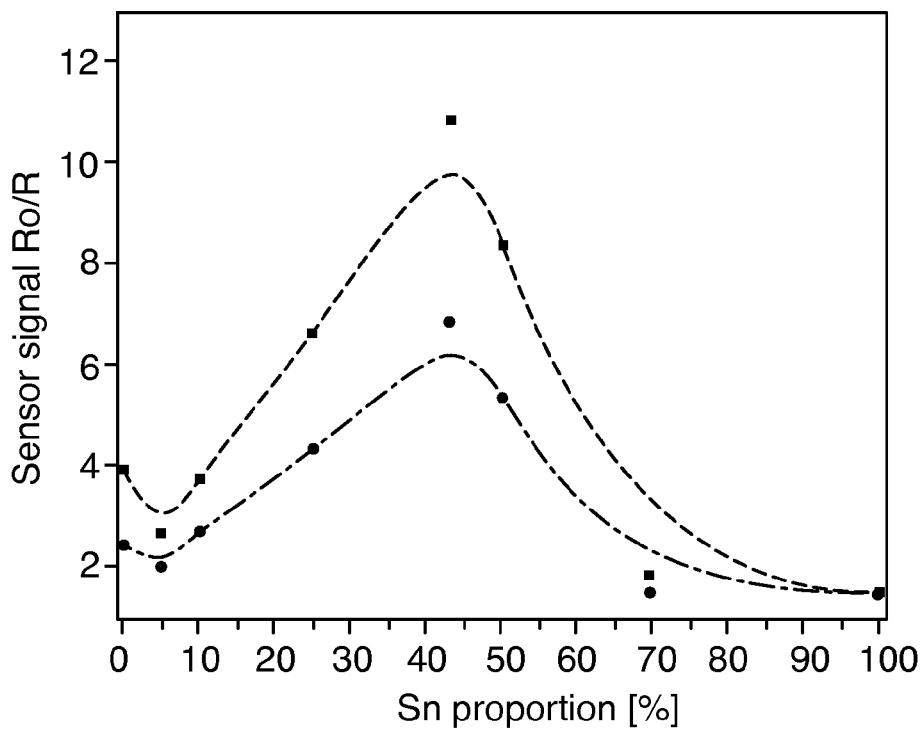

| | | | |
|---|---|---|---|
| 7,285,857 B2* | 10/2007 | Kwak et al. | 257/745 |
| 7,483,212 B2* | 1/2009 | Cho et al. | 359/586 |
| 7,507,618 B2* | 3/2009 | Dunbar | 438/197 |
| 8,329,071 B2* | 12/2012 | Wang et al. | 264/6 |
| 8,557,404 B2* | 10/2013 | Yamada et al. | 428/696 |
| 2006/0292777 A1* | 12/2006 | Dunbar | 438/197 |
| 2010/0102700 A1* | 4/2010 | Jaiswal et al. | 313/311 |
| 2011/0111215 A1* | 5/2011 | Yamada et al. | 428/336 |
| 2012/0090678 A1* | 4/2012 | Sekiguchi et al. | 136/256 |
| 2013/0111974 A1* | 5/2013 | Barsan et al. | 73/23.2 |

FOREIGN PATENT DOCUMENTS

| | | | |
|---|---|---|---|
| JP | 6170449 A | 4/1986 | |
| JP | 2010030824 A | 2/2010 | |
| JP | 2010070409 A | 4/2010 | |
| WO | 0233393 A2 | 4/2002 | |
| WO | 2004005184 A1 | 1/2004 | |
| WO | WO 2009157175 A1 * | 12/2009 | H01G 9/20 |

OTHER PUBLICATIONS

Nakayama et al., "Immobilization of aromatic aldehyde molecules on indium tin oxide surface using acetalization reaction", Thin Solid Films 518 (2009), pp. 739-742.*

Patel et al., "Indium tin oxide (ITO) thin film gas sensor for detection of methanol at room temperature", Sensors and Actuators B 96 (2003), pp. 180-189.*

Vaishnav et al., "Preparation and characterization of indium tin oxide thin films for their application as gas sensors", Thin Solid Films 487 (2005). pp. 277-282.*

Vaishnav et al., "Development of ITO thin film sensor for the detection of formaldehyde at room temperature", Sensors and Actuators B 202 (2014), pp. 1002-1009.*

Yoo et al., "Nano-grained thin-film indium tin oxide gas sensors for H2 detection", Sensors and Actuators B 108 (2005), pp. 159-164.*

Minami,Tadatsugu ,et al. "Stability of Transparent Conducting Oxide Films for Use at High Temperatures". Journal of Vacuum Science & Technology; 1999; vol. A 17; pp. 1822-1826.

* cited by examiner

GAS SENSOR AND METHOD FOR PRODUCING THE SAME

This is a National Phase Application filed under 35 U.S.C. 371 as a national stage of PCT/DE2011/001417, filed Jul. 7, 2011, an application claiming the benefit from the German patent Application DE 10 2010 027 070.9, filed Jul. 13, 2010, the content of each of which is hereby incorporated by reference in its entirety.

The present invention relates to a gas sensor for detecting gases in the air, in particular formaldehyde, as well as a method for producing said sensor.

Formaldehyde is a chemical compound industrially used in a versatile manner. It is used in the production of plastics, in the processing of wood as adhesive in plywood boards and chip boards, in the construction industry as heat insulation, in the textile industry for crease-resistant and easy-care finishing as well as in agriculture and in the food industry as a preserving agent. Formaldehyde is used as a disinfectant and is furthermore contained in cosmetics, body and mouth care products as well as sometimes in paints, varnishes and carpets (1).

Moreover, formaldehyde develops from incomplete combustion processes. For example, the latter are found in combustion engines of motor vehicles, in foundries, in the production of plastic articles or in the burning of woods in small firing systems. In the same manner, formaldehyde also develops during smoking contributing to the contamination of the air (1).

Formaldehyde is a gaseous substance which can cause health problems such as irritated eyes or mucous membrane irritations. Short-term exposure leads to irritations of the eyes and the respiratory tract even at low concentration levels: irritation of the eyes as from 0.01 ppm, irritation of the eyes and the nose as from 0.08 ppm and irritation of the throat as from 0.5 ppm. Concentrated vapors of more than 10 ppm can lead to severe irritations of the mucous membranes including lacrimation, coughing and burning in the nose and throat. Concentrations of more than 30 ppm cause toxic edema of the lungs and pneumonia with a life-threatening situation (1).

Chronic effects of formaldehyde are malaises such as insomnia, lassitude, loss of drive, lack of appetite or nervousness, eye irritations and conjunctivitis, skin irritations, chronic cough, colds and bronchitis, head ache, depressions and others. Furthermore, formaldehyde can also elicit hypersensitivities and has for some time been suspected to be able to cause cancer or to act mutagenic or teratogenic in humans. For that reason, the German Health Authority has introduced a maximum work place concentration (Maximum Allowable Concentration MAC) of 0.3 ppm (0.375 $mg/m^3$). The indoor reference value is even as low as 0.1 ppm (0.125 $mg/m^3$) since permanent exposure is to be assumed in this case (2).

For that reason, an effective and rapid detection and measurement of formaldehyde in the air is to be attached great importance.

Several methods for detecting formaldehyde in the air are known from the prior art (an overview of the known methods is given for example in the publication of H. Nishikawa and T. Sakai (3).

For example gas chromatography (GC) analysis and High-performance liquid chromatography (HPLC) analysis are analytical standard methods. For assessing occupational risks, the NIOSH (National Institute for Occupational Safety and Health) has standardized several analytical methods for detecting formaldehyde in the air.

In case of the NIOSH method 2016, for example, test air is passed through a medium composed of a silica gel that is coated with dinitrophenylhydrazine (DNPH). The chemical reaction leads to formation of hydrazones that can be identified and quantified as stable derivatives by use of HPLC, GC/FID, GC/ECD or diode array detectors (4).

The NIOSH method 2541 is based on GC/FID-analysis. Here, test air is passed through a tube coated with 2-hydroxymethylpiperidine (2-HMP). Formaldehyde of the sample reacts with 2-HMP to yield a derivative of oxazolidine which is subsequently desorbed and analyzed in a gas chromatograph (5).

The NIOSH method 3500 is based on spectrometric measurements. There is condensation of formaldehyde in the presence of sulfuric acid with 2 molecules chromotropic acid and a red carbenium cation is formed. After that, the spectroscopic verification is effected by means of a measurement at 580 nm (6).

A substantial disadvantage of the analytical methods is that the air sample needs elaborate preparation for derivatization of formaldehyde and that the actual measurement is to be effected in a special laboratory. An online detection is not feasible using these methods.

Besides the analytical methods, a number of instrumental methods is known from the prior art. Formaldehyde can be detected due to its ionization potential of 10.87 eV by means of a photo ionization detector after ionization with an argon lamp. The main disadvantage of said method lies with the great effort thereof as well.

Another method for formaldehyde detection is based on an electro-chemical cell. Said method has the drawback that the equipment required for the measurement is very expensive. Moreover, regular recalibration is required for the measuring instruments, and the life cycle of an electric cell is limited to less than one year.

Furthermore, fluorescence-based methods for detecting formaldehyde are known from the prior art, for example a detection method based on a Hanzsch reaction. Indeed, the method provides a comparatively high selectivity, but the corresponding measuring device is very expensive. Another disadvantage is the elaborate preparation of the air sample where the formaldehyde is correspondingly derivatized for the measuring (7).

The above-mentioned methods for detecting formaldehyde require high effort in equipment for derivatization and subsequent analysis of formaldehyde so that these methods can only be used in large laboratories and the results are available only after periods of long preparation times.

A MOX-based method is known from the prior art to allow even an online determination of the formaldehyde concentration. In this case, formaldehyde from the sample reacts with a metal oxide sensor which thereupon changes its conductivity. A sensitive layer of differently combined oxides of Zn, Ni, Sn, Cd, In and other metals is used as a sensor. Table 1 provides an overview of the thus far known metal oxides used for detection of formaldehyde by specification of their measuring ranges and the authors.

TABLE 1

Metal oxides known from the prior art that have been used for detecting formaldehyde.

| Ref | Year | Author | Material | Concentration [ppb] | Sensor signal [$R_0/R$] |
|---|---|---|---|---|---|
| 8 | 2001 | Dirksen | NiO | $3.9 * 10^4$-$8.0 * 10^5$ | detectable |
| 9 | 2003 | Huang | $SnO_2$ | $5.0 * 10^2$- | 2- |
| 10 | 2003 | Aronova | $SnO_2$: $WO_3$, ZnO, Pd, Pt | $1.25 * 10^3$-$1.0 * 10^5$ | 1.6- |
| 11 | 2005 | Shi | IPD $SnO_2$ | $2.0 * 10^1$-$2.0 * 10^2$ | 1.25-2.5 |
| 12 | 2005 | Zhang | $La_{0.68}Pb_{0.32}FeO_3$ | $1.0 * 10^4$-$5.0 * 10^5$ | 2-8 |
| 13 | 2006 | Lee | NiO | $1.0 * 10^3$-$1.2 * 10^4$ | 0-1.04 |
| 14 | 2006 | Xu | $ZnO/ZnSnO_3$ | $2.0 * 10^3$-$5.0 * 10^4$ | 3-34.5 |
| 15 | 2007 | Chen | $In_2O_3$: CdO | $1.0 * 10^4$-$1.0 * 10^5$ | 80-700 |
| 16 | 2007 | Huang | $LaFe_{0.77}Zn_{0.23}O_3$ | $1.0 * 10^2$-$5.0 * 10^2$ | 44.5-188.6 |
| 17 | 2007 | Lv | $SnO_2$: Au, Cu, Pt or Pd | $6.0 * 10^1$-$3.0 * 10^2$ | 1.03-1.17 |
| 18 | 2008 | Baia | ZnO:Ni | $1.0 * 10^5$- | 10- |
| 19 | 2008 | Chen | $SnO_2$—$In_2O_3$—CdO | $1.0 * 10^4$-$3.0 * 10^5$ | 40-559 |
| 20 | 2008 | Liu | $SnO_2$:Sb | $1.0 * 10^5$-$1.0 * 10^6$ | 2.5-6 |
| 21 | 2008 | Lv | $SnO_2$:NiO | $6.0 * 10^1$-$3.0 * 10^2$ | 1.03-1.17 |
| 22 | 2008 | Wang | MWCNT $SnO_2$ | $6.0 * 10^1$-$1.0 * 10^4$ | 1.02-1.6 |
| 23 | 2009 | Chu | ZnO | $1.0$-$1.0 * 10^6$ | 7.4-1000 |
| 24 | 2009 | Han | ZnO:Ga | $3.2 * 10^4$-$2.05 * 10^5$ | 2.3-9.8 |
| 25 | 2009 | Wang | $CdIn_2O_4$ | $1.0 * 10^5$-$1.0 * 10^6$ | 100-800 |
| 26 | 2009 | Wang | $SnO_2$:Pd | $3.0 * 10^1$-$1.0 * 10^4$ | 1.02-1.5 |
| 27 | 2009 | Zeng | Cd—TiO2—SnO2 | $5.0 * 10^4$-$5.0 * 10^5$ | 6-60 |

Table 1 shows that all gas sensors that are known thus far and whose functioning is based on metal oxides (except for ZnO nanowires), work at very high concentration levels that are far above the maximum reference value permitted by law, or have a low sensor signal (sensor signals that cover a concentration range of 3 orders of magnitude and that merely lie in the range of 1 to 1.6 do not allow relevant concentration grading). With reference to the nanowires, problems in the long term stability of the sensors are reported in the publication of Chu (23).

US2002/0118027A1 discloses a nano-structured anodic aluminium oxide substrate for gas sensors that has parallel pores with electrodes. The sensitive material is deposited within the pores to considerably increase the surface of the sensitive layer as compared to the planarly applied layer and thus should increase the sensitivity of the sensor. The material used for the sensitive layer plays a less important role in said document. The cost for the production of such a substrate may be comparatively high.

Therefore, the object of the present invention is to provide a novel gas sensor that has a high sensitivity that allows online detection and that can be produced at competitive cost.

According to claim 1, said object is achieved by a gas sensor that contains the material $In_4Sn_3O_{12}$ in its gas-sensitive zone. Preferred embodiments and further embodiments, the production method as well as the use thereof are subject-matter of the dependent claims.

The substance $In_4Sn_3O_{12}$ is well-known from the prior art for use in the production of radiation emitting and electrochromic devices (DE 10 2007 049 005 A1, DE 10 2004 001 508 T2, DE 00 0060 017 440 T2). Said material has not yet been described with regard to the production of sensors.

In the scope of the present invention, it surprisingly turned out that the substance $In_4Sn_3O_{12}$ possesses properties of an effective gas sensor.

It is decisive for the sensor according to the invention that the substance $In_4Sn_3O_{12}$ is present as a ternary oxide (mixed oxide phase) and not as a simple metal oxide mixture. Said material is an independent material, more exactly a non-trivial phase having its own structure. For example, this substance has been described and characterized in detail in (29). Notes or suggestions as to use the mixed oxide phase $In_4Sn_3O_{12}$ as a sensitive layer in a gas sensor cannot be taken from the prior art.

The sensor according to the invention comprises at least one gas-sensitive zone, consisting of $In_4Sn_3O_{12}$, which is preferably in the form of a layer. In the case of gas detection using the sensor according to the invention, its sensitive layer is contacted with the gas sample (e.g. air). After a reaction, the electrical properties of the sensitive layer change, a fact that can be measured as a change in the electrical impedance, the workfunction and/or capacity change. It is preferred to measure the change of the resistance.

Figure 4:
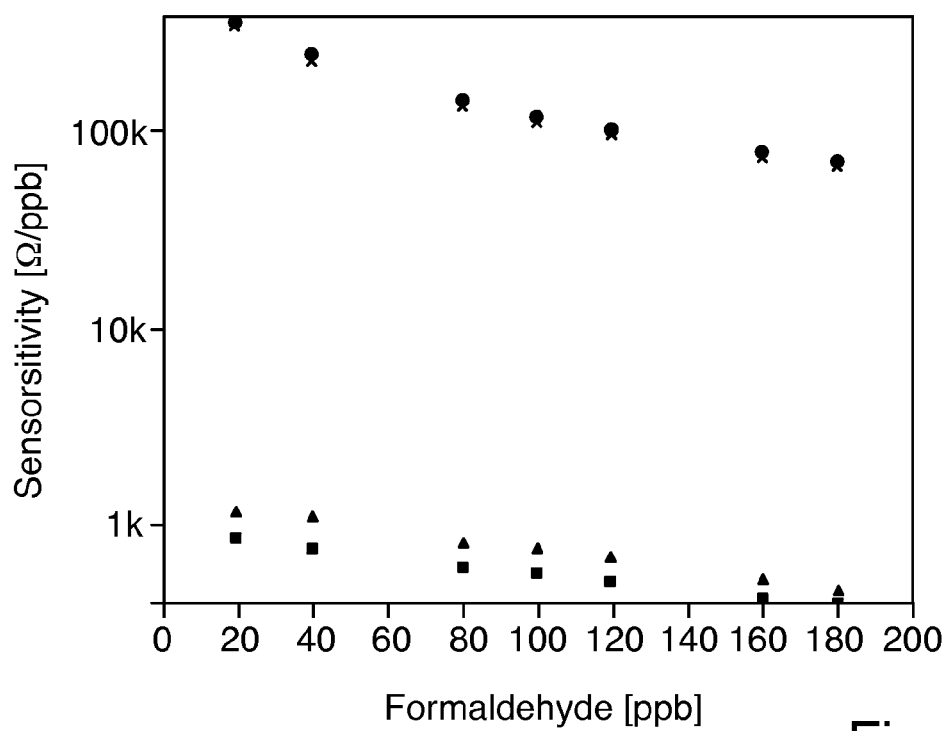

According to a preferred embodiment of the invention, the sensor according to the invention is used for detection of formaldehyde. By use of the sensor according to the invention, sensor signals ranging from 2.1 to 10.9 can be obtained for the concentration range of formaldehyde between 20 ppb and 180 ppb. Compared to the reference sensors that are commercially available, the sensor according to the invention shows an increase in the sensor signal of up to 640%. This corresponds to a sensitivity that is two orders of magnitude higher than the sensitivity of the reference sensors. While the sensitivity of the reference sensors is in the range of 1 kΩ per ppb, as shown in FIG. 4, the $In_4Sn_3O_{12}$ sensor has a sensitivity of 350 kΩ per ppb. Another advantage of the sensor according to the invention lies in its low sensitivity for CO: compared to the sensors that are commercially available, the sensor signal for CO at 100 ppb is merely 19.6%.

In a further embodiment of the invention, the sensor can be used for detecting gases such as $NO_2$, alcohol, CO and others.

The method for producing the sensor according to the invention is also a subject of the present invention. To that end, a gas-sensitive $In_4Sn_3O_{12}$ layer is applied on a substrate by means of the so-called FSP-method (flame spray pyrolysis).

The FSP-method is well-known from the prior art for the provision of a Pd/$SnO_2$ sensor (L. Mädler et al., 28). Compared to the FSP-method, the inventive step of the present method consists in the identification of suitable source substances in order to be able to produce a $In_4Sn_3O_{12}$ layer. In the scope of the present invention it turned out that when using organometallic compounds of indium or tin as source materials, dissolved in an organic solvent, particularly good results can be achieved in the production of the sensitive layer. In particular the substances indium acetylacetone and tin-2-ethylhexanoate, dissolved in xylene, are suitable for producing $In_4Sn_3O_{12}$ layers.

Furthermore it turned out that the concentrations of the source substances play an important role in the method for producing the gas-sensitive layer for the sensor according to the invention. The best results were achieved when the source substances indium acetylacetone and tin-2-ethylhexanoate were used in each case at a concentration between 0.05 and 0.7 molar (mol per liter of solvent).

Another subject of the present invention is the use of the above described gas sensor for detecting gas in home environments in order to allow online analysis of a corresponding contamination of the air. Furthermore, the sensor is adapted to allow an air analysis in business establishments where formaldehyde is handled and thus an exposure of humans and environment cannot be excluded.

Since to date there has not been a possibility for detecting formaldehyde by an online application, the sensor according to the invention is a novel milestone with regard to the prior art.

Further advantages, features and application possibilities of the sensor and the method for producing the same are described subsequently by means of the embodiments described below with reference to the figures.

FIG. 1: shows the sensor signal of the sensor according to the invention depending on the tin concentration. 0% corresponds to pure $In_2O_3$, 100% corresponds to pure $SnO_2$. A maximum sensor signal is achieved at a Sn proportion of 43% which corresponds to the pure phase $In_4Sn_3O_{12}$. Squares designate sensor signals at a formaldehyde concentration of 180 ppb, dots designate sensor signals at a concentration of 100 ppb.

Figure 2:
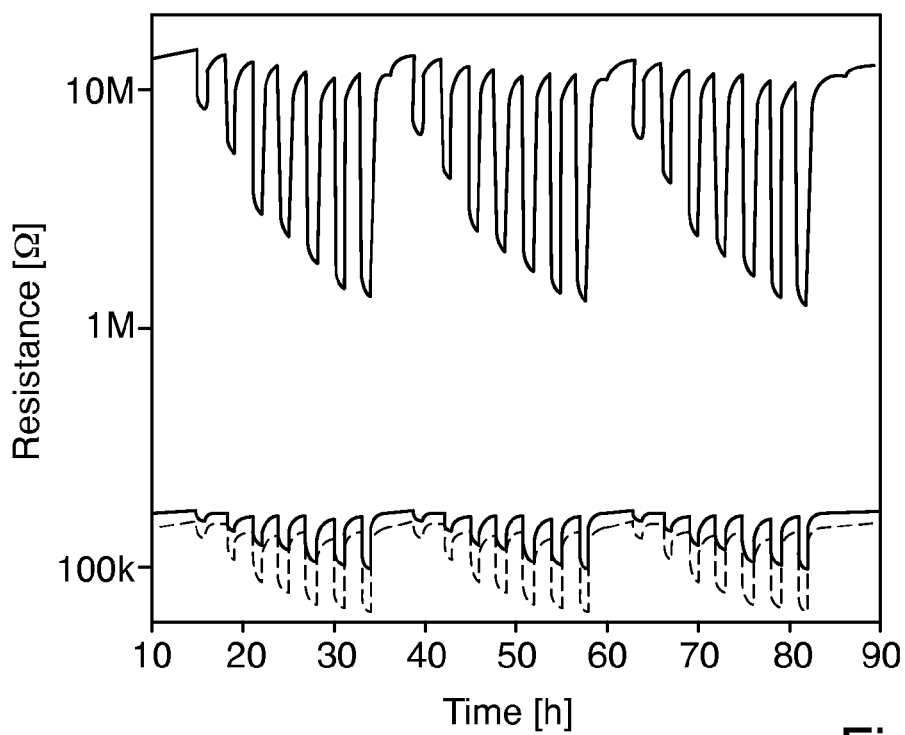

FIG. 2: shows as a function of time the curve of the resistance for measurements of different formaldehyde concentrations with the sensor according to the invention compared to measurements of devices that are known from the prior art. The solid line corresponds to the measurement of the sensor according to the invention having the pure $In_4Sn_3O_{12}$ phase, the dotted line corresponds to the AppliedSensor MLC (2.3 V) and the dashed line corresponds to the Figaro TGS 2620 (5.0 V) sensor. Due to the logarithmic plotting it can be discerned by direct, visual comparison that the sensor signal for the sensor according to the invention is significantly bigger than the signal of the sensors known from the prior art. The concentrations to be correlated to the individual signal steps are 20, 40, 80, 100, 120, 160 and 180 ppb, then the sequence is repeating.

Figure 3:
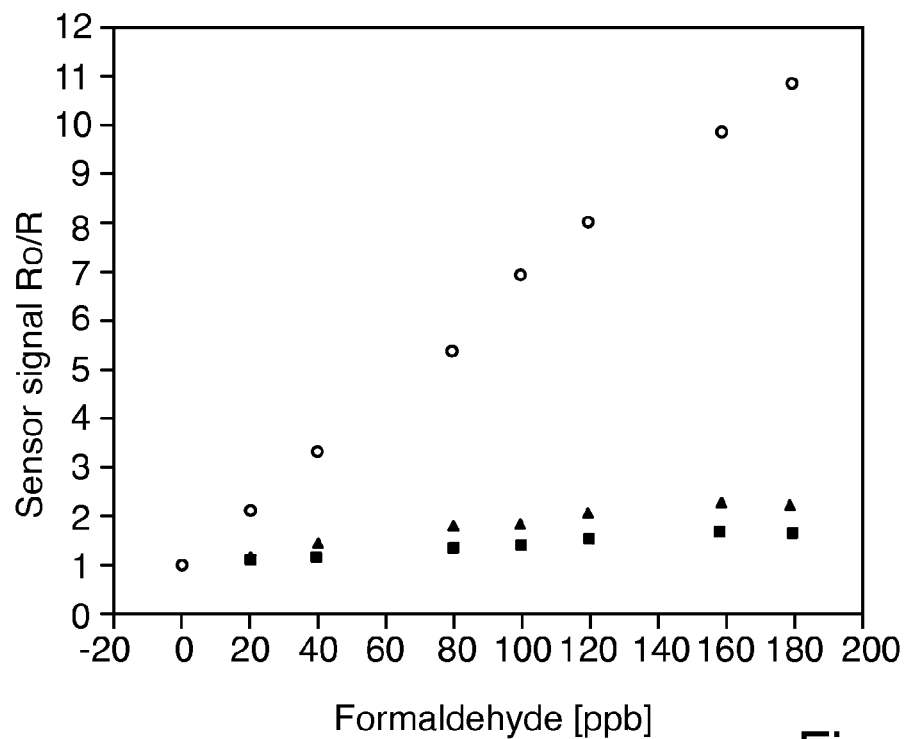

FIG. 3: shows as a function of time the curve of the sensor signal at different concentrations of formaldehyde in humid air (50% relative humidity). The enhanced sensor signal of the $In_4Sn_3O_{12}$ phase (circles) compared to the sensor signals measured by the reference sensors from Figaro (squares) and AppliedSensor (triangles) that are known from the prior art is clearly discernible in every concentration area. Both the reference sensors well-known from the prior art are operative, similar to the sensor according to the invention, based on a change in resistance, but their sensitive layer is based on tin dioxide.

FIG. 4: shows the sensitivity of the sensor according to the invention compared to the two reference sensors that are well-known from the prior art. Squares correspond to the Figaro TGS 2620, triangles correspond to the AppliedSensor MLC and dots or asterisks indicate the sensitivity of the $In_4Sn_3O_{12}$ sensor according to the invention on two different days. According to the definition of sensitivity, here the change of the resistance relative to the change in the analyte concentration is plotted against the analyte concentration. It is clearly discernible that the sensor according to the invention has a sensitivity that is two orders of magnitude higher than the sensitivity of the reference sensors known from the prior art.

Examples of Embodiments

Preparation of Material and Deposition on the Sensor Substrate

In view of the phase diagram of the solid solution of $SnO_2$ in $In_2O_3$ (I. Isomäki et al. (29)), it is in evidence that the phase $In_4Sn_3O_{12}$ is a metastable high-temperature phase that forms in a temperature range of around 1600 to 1900 K. If the temperature is lowered slowly (go down vertically in the diagram), the phase breaks down into a solid solution of ITO (indium tin oxide) and $SnO_2$. In case of compositions having a Sn content of more than 10%, the $In_4Sn_3O_{12}$ can always be obtained by selection of a suitable temperature. If the temperature is increased even more, finally an ionic fluid is formed. The synthesis method of flame spray pyrolysis thus allows preparation of the phase in the flame and deposition onto a cooled substrate ensures that said phase is quenched and thus is maintained.

Organometallic compounds such as indium acetylacetone (99.9% pure, Strem) or tin-2-ethylhexanoate (99.5% pure, Strem) were used in the flame spray pyrolysis (FSP) in order to produce tin-doped $In_2O_3$ (ITO) metal oxides. The organometallic compounds, in the following referred to as precursors, were dissolved in organic solvents (for example toluene (99.95% pure, Strem) or xylene (99.99% pure, Sigma Aldrich)) in order to obtain concentrations of 0.15 M. A volume flow of the precursors of 5 ml/min was defined as default parameter during the synthesis. The solutions were atomized by means of a nozzle and an oxygen volume flow of 5 l/min streaming in parallel, with an atomizing pressure of 1.6 bars at the nozzle. The combustion of the precursor spray was injected by a circular methane/oxygen flame (1.5 l/min/3.2 l/min).

The composition of the synthesized phase can be seen from table 2. Depending on the ratio of the precursors used, compositions of the sensitive layer can thus systematically be obtained. The table shows that the pure $In_4Sn_3O_{12}$-phase is present at a tin concentration of 43%.

The sensor substrates (Hereaus) were placed at a distance of 25 cm above the flame and water-cooled on their rear side by a corresponding sample holder. The deposition time was 20 minutes.

TABLE 2

Measured values of envisioned tin concentrations and the composition of the material obtained.

| Sn/(Sn + In) | Mass % of $SnO_2$ or ITO | | Mass % of $In_4Sn_3O_{12}$ | |
|---|---|---|---|---|
| [%] Nominal | expected | Detected (XRD) | expected | Detected (XRD) |
| 0 | 100 | Not measured | | Not measured |
| 5 | 100 | 100 | 0 | 0 |
| 10 | 89 | 96 | 11 | 4 |
| 17 | 70 | 77 | 30 | 23 |
| 25 | 48 | 49 | 52 | 51 |
| 43 | 0 | 0 | 100 | 100 |
| 50 | | 2 | | 98 |
| 60 | | 6 | | 94 |

TABLE 2-continued

Measured values of envisioned tin concentrations and the composition of the material obtained.

| Sn/(Sn + In) | Mass % of SnO$_2$ or ITO | | Mass % of In$_4$Sn$_3$O$_{12}$ | |
|---|---|---|---|---|
| [%] Nominal | expected | Detected (XRD) | expected | Detected (XRD) |
| 70 | | 47 | | 53 |
| 80 | | 93 | | 7 |
| 100 | 100 | 100 | 0 | 0 |

Measuring of Resistance and Temperature Calibration

The substrates are heated in an oven and the resistance of the heating coil on the rear side is determined. The developing calibration curve is used as a basis for operating the sensor.

The sensors are entered into corresponding measuring chambers which are connected to a special gas mixing device (Röck et al. (30)) that has been developed especially for the working with small concentrations of formaldehyde. The resistance of the sensitive layer is read out by a multimeter (Agilent 34970A) which ensures the collection of measuring data in combination with a computer. FIG. 2 shows as a function of time the curve of a resistance measurement. Said data can be transformed by mathematical operations into the terms sensor signal and sensitivity, in order to get a rough indication about the quality of a sensor for a certain application. In FIG. 1, the sensor signals of the different compositions of the sensitive layers are indicated. For a composition with a Sn proportion of 43%, said data can directly be taken from the curve of the sensor signal shown in FIG. 3.

REFERENCES

1. WHO Regional Office for Europe, Copenhagen, 2001 http://test.cp.euro.who.int/document/aig/5_8formaldehyde.pdf
2. Bundesinstitut für Risikobewertung, Toxikologische Bewertung von Formaldehyd vom 30.03.2006, http://www.b-fr.bund.de/cm/252/toxikologische_bewertung_von_formaldehy d.pdf
3. H. Nishikawa, T. Sakai, Derivatization and Chromatographic Determination of Aldehydes in Gaseous and Air Samples, Journal of Chromatography A, vol. 710, pp. 159-165, 1995
4. NIOSH Manual of Analytical Methods, Formaldehyde: Method 2016, 4$^{th}$ Edition, 2003, http://www.cdc.gov./niosh/docs/2003-154/pdfs/2016.pdf
5. NIOSH Manual of Analytical Methods, Formaldehyde: Method 2541, 4th Edition, 2003, http://www.cdc.gov./niosh/docs/2003-154/pdfs/2541.pdf
6. NIOSH Manual of Analytical Methods, Formaldehyde: Method 3500, 4th Edition, 2003, http://www.cdc.gov./niosh/docs/2003-154/pdfs/3500.pdf
7. VdL RL-03, VdL-Richtlinie Formaldehydbestimmung, 1997, http://www.lackindustrie.de/template_downloads/tmp_LackverbandInterne t/79811VDLRL03-597.pdf?DokNr=79811&p=16
8. James A. Dirksen, Kristin Duval, Terry A. Ring, NiO thin-film formaldehyde gas sensor, Sensors and Actuators B: Chemical, Volume 80, Issue 2, 20 Nov. 2001, Pages 106-115, ISSN 0925-4005, DOI: 10.1016/S0925-4005(01)00898-X
9. Xingjiu Huang, Fanli Meng, Zongxin Pi, Weihong Xu, Jinhuai Liu, Gas sensing behavior of a single tin dioxide sensor under dynamic temperature modulation, Sensors and Actuators B: Chemical, Volume 99, Issues 2-3, 1 May 2004, Pages 444-450, ISSN 0925-4005, DOI: 10.1016/j.snb.2003.12.013
10. Liqin Shi, Wei Gao, Yuki Hasegawa, Teruaki Katsube, Mamoru Nakano, Kiyozumi Nakamura, High Sensitive Formaldehyde Gas Sensor Prepared by R.F. Induction Plasma Deposition Method. IEEJ Transactions on Sensors and Micromachines, 2005. 125(12): p.485-489.
11. Ling Zhang, Jifan Hu, Peng Song, Hongwei Qin, Xiangdong Liu, Minhua Jiang, Formaldehyde-sensing characteristics of perovskite La0.68Pb0.32FeO3 nano-materials, Physica B: Condensed Matter, Volume 370, Issues 1-4, 15 Dec. 2005, Pages 259-263.
12. Chia-Yen Lee, Che-Ming Chiang, Yu-Hsiang Wang, Rong-Hua Ma, A self-heating gas sensor with integrated NiO thin film for formaldehyde detection, Sensors and Actuators B: Chemical, Volume 122, Issue 2, 26 Mar. 2007, Pages 503-510, ISSN 0925-4005, DOI: 10.1016/j.snb.2006.03.033.
13. Jiaqiang Xu, Xiaohua Jia, Xiangdong Luo, Guaxi Xi, Jianjun Han, Qiaohuan Gao, Selective detection of HCHO gas using mixed oxides of ZnO/ZnSnO3, Sensors and Actuators B: Chemical, Volume 120, Issue 2, 10 Jan. 2007, Pages 694-699, ISSN 0925-4005, DOI: 10.1016/j.snb.2006.03.033.
14. T. Chen, Q. J. Liu, Z. L. Zhou, Y. D. Wang, The fabrication and gans-sensing characteristics of the formaldehyde gas sensor with high sensitivity, Sensors and Actuators B: Chemical, Volume 131, Issue, Special Issue: Selected Papers from the 12$^{th}$ International Symposium on Olfaction and Electronic Noses—ISOEN 2007, International Symposium on Olfaction and Electronic Noses, 14 Apr. 2008, Pages 301-305, ISSN 0925-4005, DOI: 10.1016/j.snb.2007.11.025
15. Shanxing Huang, Hongwei Qin, Peng Song, Xing Liu, Lun Li, Rui Zhang, ifan Hu, Hongdan Yan, Minhzua Jiang, The formaldehyde sensitivity of LaFel-x Zn x 03-based gas sensor. Journal of Materials Science, 2007. 42(24): p. 9973-9977.
16. Pin Lv, Zhenan Tang, Guangfen Wei, Jun Yu, Zhengxing Huang, Recognizing indoor formaldehyde in binary gas mixtures with a micro gas sensor array and a neural network. Measurement Science and Technology, 2007. 18(9): p. 2997.
17. Zikui Bai, Changsheng Xie, Mulin Hu, Shunping Zhang, Formaldehyde sensor based on Ni-doped tetrapod-shaped ZnO nanopowder induced by external magnetic field. Physica E: Low-dimensional Systems and Nanostructures, 2008. 41(2): p. 235-239.
18. T. Chen, Q. J. Liu, Z. L. Zhou, Y. D. Wang, A high sensitivity gas sensor for formaldehyde based on CdO and In 2 O 3 doped nanocrystalline SnO2. Nanotechnology, 2008. 19(9): p. 095506.
19. Jinyun Liu, Zheng Guo, Fanli Meng, Yong Jia, Jinhuai Liu, A novel Antimony-Carbon Nanotube-Tin Oxide Thin Film: Carbon Nanotubes as Growth Guider and Energy Buffer. Application for Indoor Air Pollutants Gas Sensor. The Journal of Physical Chemistry C, 2008. 112(15): p. 6119-6125.
20. Pin Lv, Zhen A. Tang, Jun Yu, Feng T. Zhang, Guang F. Wie, Zheng X. Huang, Yann Hu, Study on a micro-gas sensor with SnO2-Nio sensitive film for indoor formaldehyde detection. Sensors and Actuators B: Chemical, 2008. 132(1): p. 74-80.

21. Jing Wang, Li Liu, Song-Ying Cong, Jin-Qing Qi, Bao-Kun Xu, An enrichment method to detect low concentration formaldehyde. Sensors and Actuators B: Chemical, 2008. 134(2): p. 1010-1015.
22. Xiangfeng Chu, Tongyun Chen, Wangbing Zhang, Banqiao Zheng, Hengfu Shui, Investigation on formaldehyde gas sensor with ZnO thick film prepared through microwave heating method. Sensors and Actuators B: Chemical, 2009. 142(1): p. 49-54.
23. Ning Han, Yajun Tian, Xiaofeng Wu, Yunfa Chen, Improving humidity selectivity in formaldehyde gas sensing by a two-sensor array made of Ga-doped ZnO. Sensors and Actuators B: Chemical, 2009. 138(1): p. 228-235.
24. Yude Wang, Ting Chen, Quiying Mu, Guofeng Wangm A nonaqueous sol-gel route to synthesize CdIn2O4 nanoparticles for the improvement of formaldehyde-sensing performance, Scripta Materialia, Volume 61, Issue 10, November 2009, Pages 935-938, ISSN 1359-6462, DOI: 10.1016/j.scriptamat.2009.07.029.
25. Jing Wang, Peng Zhang, Jin-Qing Qi, Peng-Jun Yao, Silicon-based micro-gas sensors for detecting formaldehyde, Sensors and Actuators B: Chemical, Volume 136, Issue 2, 2 Mar. 2009, Pages 399-404, ISSN 0925-4005, DOI: 10.1016/j.snb.2008.12.056.
26. Zeng W., Liu T., Wang Z., Tsukimoto S., Saito M., Ikuhara Y. Selective Detection of Formaldehyde Gas Using a Cd-Doped $TiO_2$—$SnO_2$ Sensor. Sensors. 2009; 9(11):9029-9038
27. M. A. Aronova, K. S. Chang, I. Takeuchi, H. Jabs, D. westerheim, A. Gonzalez-Martin, J. Kim, B-Lewis, Combinatorial libraries of semiconductor gas sensors as inorganic electronic noses—Appl. Phys. Lett. 83, 6, 1255-1257.
28. L. Mädler, A. Rössler, S. E: Pratsinis, T. Sahm, A. Curio, N. Barsan, U. Weimar. Sensors and Actuators B 114 (2206) 283-295.
29. I. Isomäki, M. H., W. Gierlotka, B. Onderka, K. Fitzner, Thermodynamic evaluation of the In—Sn—O system. Journal of Alloys and Compounds, 2006(422): p. 173-177.
30. F. Röck, N. Barsan, U. Weimar, vorgelegt bei "Measurement Science and Technology", 2010.

The invention claimed is:
1. A sensor for detecting gases, comprising at least one gas-sensitive zone applied on a substrate, characterized in that the gas-sensitive zone comprises a metastable mixed oxide phase of $In_4Sn_3O_{12}$ applied using flame spray pyrolysis (FSP).
2. The sensor according to claim 1, characterized in that the at least one gas-sensitive zone is in the form of a layer.
3. A method for producing a sensor according to claim 1, wherein the production of the gas-sensitive zone is effected by means of a flame spray pyrolysis (FSP).
4. The method according to claim 3, characterized in that organometallic compounds of indium and tin, dissolved in an organic solvent, are used as source materials.
5. The method according to claim 3, characterized in that the source materials are indium acetylacetone or tin-2-ethylhexanoate.
6. The method according to claim 5, characterized in that the source materials indium acetylacetone or tin-2-ethylhexanoate are in each case used in the same concentrations between 0.05 and 0.7 mol.
7. Use of the sensor according to claim 1 for online gas detection.
8. Use of the sensor according to claim 1 for detecting formaldehyde.
9. Use of the sensor according to claim 1 for detecting gas in the home environment or in business establishments.

* * * * *

UNITED STATES PATENT AND TRADEMARK OFFICE
CERTIFICATE OF CORRECTION

PATENT NO. : 9,091,669 B2
APPLICATION NO. : 13/809631
DATED : July 28, 2015
INVENTOR(S) : Nicolae Barsan et al.

It is certified that error appears in the above-identified patent and that said Letters Patent is hereby corrected as shown below:

Title Page

Correct Item (73) the Assignees' name and city to read:
1) EBERHARD KARLS UNIVERSITÄT TÜBINGEN, Tübingen (DE)
2) UNIVERSITÄT BREMEN, Bremen (DE)

Signed and Sealed this
Twenty-sixth Day of January, 2016

Michelle K. Lee
*Director of the United States Patent and Trademark Office*